(12) United States Patent
Yu et al.

(10) Patent No.: US 6,221,340 B1
(45) Date of Patent: Apr. 24, 2001

(54) ZINC CONTAINING DENTIFRICE COMPOSITIONS

(75) Inventors: Dahshen Yu, Randolph; Rita M. Parikh, Paramus; Charles Pozzi, Denville; Bruce Kohut, Toms River, all of NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/288,828

(22) Filed: Apr. 8, 1999

(51) Int. Cl.[7] ............... A61K 7/16; A61K 7/18
(52) U.S. Cl. ............................. 424/49; 424/52
(58) Field of Search .......................... 424/49–58

(56) References Cited

U.S. PATENT DOCUMENTS

| | | | | |
|---|---|---|---|---|
| 4,100,269 | * | 7/1978 | Pader | 424/49 |
| 4,309,409 | * | 1/1982 | Coll-Palagos et al. | 424/52 |
| 4,416,867 | * | 11/1983 | Ritchey et al. | 424/49 |
| 4,425,325 | * | 1/1984 | Ritchey et al. | 424/54 |
| 4,545,979 | * | 10/1985 | Ambike et al. | 424/49 |
| 4,550,018 | * | 10/1985 | Ambike et al. | 424/49 |
| 4,568,540 | * | 2/1986 | Asano et al. | 424/52 |
| 4,774,078 | * | 9/1988 | Curtis et al. | 424/52 |
| 4,945,087 | * | 7/1990 | Talwar et al. | 424/49 |
| 5,059,416 | * | 10/1991 | Cherukuri et al. | 424/49 |
| 5,066,483 | * | 11/1991 | Harkrader et al. | 424/49 |
| 5,085,850 | * | 2/1992 | Pan et al. | 424/49 |
| 5,094,834 | | 3/1992 | Mazzanobile et al. | |
| 5,298,238 | * | 3/1994 | Hussein et al. | 424/49 |
| 5,723,106 | * | 3/1998 | Buch et al. | 424/49 |
| 5,811,079 | * | 9/1998 | Yu et al. | 424/52 |
| 5,817,295 | * | 10/1998 | Chauditari et al. | 424/49 |
| 5,874,068 | * | 2/1999 | Engelman et al. | 424/54 |
| 5,891,422 | * | 4/1999 | Pan et al. | 424/49 |
| 5,942,211 | * | 8/1999 | Harper et al. | 424/49 |
| 5,948,390 | * | 9/1999 | Nelson et al. | 424/54 |

FOREIGN PATENT DOCUMENTS

| | | |
|---|---|---|
| 834131 | 2/1970 | (CA) . |
| WO9603109 | 2/1996 | (WO) . |
| 97/40812 * | 11/1997 | (WO) . |
| 98/11867 * | 3/1998 | (WO) . |

* cited by examiner

Primary Examiner—Shep K. Rose
(74) Attorney, Agent, or Firm—Darryl C. Little; Evan J. Federman

(57) ABSTRACT

A zinc containing, low pH dentifrice composition provides better bioavailability of the zinc by incorporating a buffer system.

4 Claims, No Drawings

ZINC CONTAINING DENTIFRICE COMPOSITIONS

BACKGROUND OF THE INVENTION

1. Field of the Invention

The present invention relates to zinc containing anticalculus dentifrice compositions. Specifically, the invention is directed to low pH dentifrice compositions employing one or more slightly soluble zinc compounds as the active agent. Even more specifically, the dentifrice compositions according to the present invention significantly enhance the bioavailability of zinc.

2. Description of Related Art

Zinc compositions have been added to dentifrice compositions for controlling calculus. See for example, U.S. Pat. No. 4,100,269 to Pader.

PCT Application WO 96/03109 to Warner-Lambert Company teaches an antiseptic, anticaries dentifrice having a pH of about 3.0 to about 5.5. Acidifiers, including phosphoric acid, acidic phosphate salts, benzoic acid and food grade acids, such as citric acid, acidify the dentifrice. The dentifrice may also be buffered by salts of the acids such as citric acid-sodium citrate, phosphoric acid-sodium phosphate, sodium monobasic phosphate-sodium dibasic phosphate, acetic acid-sodium acetate, and benzoic acid and benzoate.

U.S. Pat. Nos. 4,545,979 and 4,550,018 to Ambike et al. teach a dental hygiene composition in an acidic pH range of from 3.0 to 5.0, pH buffers, fluoride, thymol, eucalyptol, methyl salicylate, peppermint and spearmint oil flavors, and 0.1 to 2.0 percent by weight of one or more highly pure alkali metal salts of dodecyl sulphate having less than 5% non-dodecyl alkyl sulphate salts.

Canadian Patent No. 834131 to Tisserand teaches a dentifrice preparation that has an acidic pH of about 3.8 to 5.8, optimally a pH of 4.0 to 5.5, and most preferably a pH of 4.0 to 4.8; fluoride; and contains flavor oils such as menthol, methyl salicylate or thyme oil and other flavors such that the composition is substantially free of hydrocarbon terpenes. According to Tisserand when essential oils which are not free of terpenes are employed in a fluoride dentifrice which has a pH in the range of about 3.8 to 5.8 the flavor develops a pronounced rancid and sour taste in a period of less than 3 months.

While the prior art discloses low pH toothpaste and other dentifrice compositions that contain zinc, there is a need for dentifrice compositions that deliver enhanced bioavailable zinc so that the effective zinc content can be lowered. It is believed that the zinc compounds tend to be astringent. Therefore, reducing the zinc content in the product can improve the consumer acceptability of the product.

SUMMARY OF THE INVENTION

The present invention is directed to dentifrice compositions including one or more slightly soluble zinc compounds. The term slightly soluble means that the zinc compound is not more than about 0.5% w/w soluble in water. The dentifrice compositions according to the present invention also include a buffer system; and an oral vehicle, wherein the dentifrice composition has a pH from about 3.0 to about 5.5, the zinc compound is in an amount sufficient to provide at least about 2000 ppm of zinc ion and the amount of zinc ion that is bio-available is at least about 1000 ppm.

The dentifrice compositions according to the present invention contain zinc ions and a buffering agent that produces a significantly and unexpectedly enhanced bioavailablity of zinc.

DETAILED DESCRIPTION OF PREFERRED EMBODIMENTS

The dentifrice compositions according to the present invention include a zinc source. Zinc in known to help prevent tartar in the oral cavity. The zinc compounds that can be used in the present invention include

| | |
|---|---|
| Zinc Bacitracin | Zinc Oxide |
| Zinc Citrate | Zinc Peroxide |
| Zinc Tribromosalicylanilide | Zinc Phosphate |
| Zinc Carbonate | Zinc Pyrophosphate |
| Zinc Fluoride | Zinc Silicate |
| Zinc Formate | Zinc Stearate |
| Zinc Lactate | Zinc Tannate |
| Zinc Oleate | Zinc Oxalate |
| | Zinc Chloride |

Preferred salts are zinc citrate, zinc oxide, zinc pyrophosphate, and zinc silicate. The most preferred salt is zinc citrate.

The zinc salt is added to the composition in an amount sufficient to provide zinc ions in an amount from about 0.01 to about 1.0% w/w of the composition. Preferably the amount of zinc salt added to the composition is sufficient to provide zinc ions in an amount from about 0.02 to about 0.7% w/w of the composition. More preferably, the amount of zinc salt added to the composition is sufficient to provide zinc ions in an amount from about 0.05 to about 0.5% w/w of the composition. Even more preferably, the amount of zinc salt added to the composition is sufficient to provide zinc ions in an amount from about 0.1 to about 0.3% w/w of the composition.

The amount of zinc salt added to the compositions should be sufficient to provide the amounts of zinc ion listed above. The exact amount of zinc salt used can be readily determined to one of ordinary skill in the art and is dependent upon the salt used.

The pH for the preferred embodiment according to the present invention is from about 3.0 to about 5.5. A pH greater than about 5.5 has been found to decrease the antiseptic activity of the dentifrice composition.

The pH of the claimed dentifrice is adjusted to below 5.5 using suitable food or pharmaceutical grade acidifiers. These could include, but are not limited to, one or a combination of the following: phosphoric acid, benzoic acid, citric acid, or other tricarboxylic acids, and the like. The most preferred acidifiers in the present invention include a mixture of phosphoric acid from about 0.01% w/w to about 3.0% w/w, preferably in the range of from about 0.1% w/w to about 1.5% w/w, and most preferably in the range of from about 0.2% w/w to about 0.75% w/w; monobasic sodium phosphate from about 0.01% w/w to about 1% w/w, preferably from about 0.1% w/w to about 0.5% w/w, and most preferably from about 0.2% w/w to about 0.4% w/w; dibasic sodium phosphate from about 0.001% w/w to about 1.0% w/w, preferably from about 0.01% w/w to about 0.5% w/w, and most preferably from about 0.01% w/w to about 0.05% w/w; and benzoic acid in the range of from about 0.01% w/w to about 1.0% w/w, preferably from about 0.05% w/w to about 0.5% w/w, and most preferably from about 0.08% w/w to about 0.35% w/w. The exact amount of acidifier added will depend on the final pH and buffer capacity desired.

The pH of the products may be buffered with salts of the acids in question. Common buffer systems include phosphoric acid and sodium phosphate salts, or citric acid and sodium citrate. Suitable buffers for use in this invention include citric acid-sodium citrate, phosphoric acid-sodium phosphate, sodium monobasic phosphate, sodium dibasic phosphate, acetic acid-sodium acetate, succinic acid-sodium succinate, aconitic acid-sodium aconitate and benzoic acid-sodium benzoate in amounts up to about 1% w/w, preferably from about 0.05% w/w to about 0.75% w/w of the composition, and most preferably from about 0.1% w/w to about 0.5% w/w of the composition.

The dentifrice compositions according to the present invention contain anti-microbial agents and one or more fluoride-releasing compounds that provide anticaries activity. Dentifrice compositions of this invention also contain, but are not limited to, one or more of the following dentifrice additives: abrasives, surfactants, binders and thickeners, humectants, sweeteners, desensitizing agents, flavors, colors, and preservatives. The preceding active ingredients and additives are combined in a hydrous or anhydrous vehicle to form a solid (i.e. toothpowder), a semi-solid (i.e. paste or gel), or a liquid.

The present invention may also include an anti-microbial agent. One class of anti-microbial agent known for use in dentifrice is the non-cationic anti-microbial agent. A substantially water-insoluble anti-microbial agent has a solubility in water at 25° C. of less than 1%, preferably less than 0.5% and more preferably less than 0.1%. The anti-microbial agents employed in dentifrice compositions of this invention can be regarded as essentially non-ionic in character. However, many suitable anti-microbial compounds contain one or more phenolic hydroxy groups that may be ionisable at certain pHs. A more exact description of the general class of anti-microbial agents useful in the dentifrice composition of this invention is that they are non-cationic in nature.

Examples of classes of non-cationic anti-microbial agents that may be employed in the dentifrice composition of the invention are the phenolic and bisphenolic compounds, halogenated diphenyl ethers, benzoate esters and carbanilides.

Illustrative of the phenolic anti-microbial compounds, which include the halogenated salicylanilides, are 2-phenylphenol, 4-chlorophenol, 4-chloro-2-methylphenol, 4-chloro-3-methylphenol, 4-chloro-3,5-dimethylphenol, 2,4-dichloro-3,5-dimethylphenol, 3,4,5,6-tetrabromo-2-methylphenol, 5-methyl-2-pentylphenol, 4-isopropyl-3-methylphenol, 5-chloro-2-hydroxydiphenylmethane, 4',5-dibromosalicylanilide, 3,4',5-trichlorosalicylanilide, 3,4',5-tribromosalicylanilide, 2,3,3',5-tetrachlorosalicylanilide, 3,3',4,5'-tetrachlorosalicylanilide, 3,5-dibromo-3'-trifluoromethylsalicylanilide, 5-n-octanoyl-3'-trifluoromethylsalicylanilide.

Among the bisphenolic compounds may be mentioned 2,2'-methylenebis(3,4,6-trichlorophenol), 2,2'-methylenebis(4-chlorophenol), 2,2'-methylenebis(4-chloro-6-bromophenol), bis(2-hydroxy-3,5-dichlorophenyl) sulphide, bis(2-hydroxy-5-chlorophenyl) sulphide.

These antibacterial agents may be employed in the form of their zinc derivatives, many of which are disclosed in U.S. Pat. No. 4,022,880.

Exemplifying the class of the halogenated hydroxydiphenyl ethers are the compounds 2',4,4'-trichloro-2-hydroxydiphenyl ether and 2,2'-dihydroxy-5,5'-dibromo-diphenyl ether.

Another well-known class of non-cationic anti-microbial agents are the esters of p-hydroxybenzoic acid, especially the methyl, ethyl, propyl, isopropyl, butyl, isobutyl, hexyl, heptyl and benzyl esters.

Halogenated carbanilides can also be used, which class is typified by 3,4,4'-trichlorocarbanilide, 3-trifluoromethyl-4,4'-dichlorocarbanilide, 3,3',4-trichlorocarbanilide.

Other known substantially water-insoluble non-cationic anti-microbial agents can also be used, for example 2,4-dichlorobenzyl alcohol, 3,4-dichlorobenzyl alcohol and 3-(4-chlorophenoxy)-propan-1,2-diol.

The above-mentioned anti-microbial agents that are suitable for use in dentifrices are not antibiotics. Antibiotics are not generally used so as to avoid the risk of resistant strains of bacteria developing. The anti-microbial agent will usually be used in an amount of 0.01 to 5%, preferably 0.05 to 1% by weight of the dentifrice. A mixture of anti-microbial agents may of course be used.

The dentifrice compositions according to the present invention can also include essential oils. Essential oils are volatile aromatic oils that are synthetic or are derived from plants by distillation, expression or extraction. Essential oils usually carry the odor or flavor of the plant from which they are obtained. If used in the dentifrice compositions of this invention, essential oils provide anti-gingivitis activity. Some of these essential oils also act as flavoring agents. The essential oils of this invention include, but are not limited to, thymol, menthol, methyl salicylate (wintergreen oil) and eucalyptol. Thymol, also known by the chemical formula 5-methyl 2-(1-methylethyl) phenol, is obtained from the essential oil of *Thymus vulgaris Labiatae* and *Monarda punctata Labiatae*. Thymol is a white crystalline powder with an aromatic odor and taste. Thymol is soluble in organic solvents but only slightly soluble in deionized water.

Menthol is isolated principally from the oil of *Mentha arvensis*. In its commercial form, menthol is available as L-menthol crystals obtained from a process involving cooling of the oil. Fractional distillation of peppermint oil that usually contains from about 40% to about 65% menthol represents another important source of menthol. Synthetic sources of L-menthol are also available.

Eucalyptol is derived from the eucalyptus tree. Having a camphoraceous odor and cooling taste, this essential oil is often combined with other essential oils such as menthol in confection formulations to impart medicinal effect. Combinations of menthol and eucalyptol are widely used. Particularly preferred uses of the menthol-eucalyptol combination include, according to the present invention, dentifrices such as toothpastes or dental gels.

Methyl salicylate is the main ingredient in many essential oils, constituting about 99% of oil of wintergreen (*Gaultheria procumbens*) and sweet birch (*Betula lenta*). Methyl salicylate, which has a distinctive refreshing aroma, is used widely in mouthwashes, chewing gums and other oral and pharmaceutical preparations.

The amounts of essential oils that can be used in the dentifrice compositions of the present invention are from about 0.46% to about 0.5623% thymol, about 0.4644% to about 0.5676% methyl salicylate, about 0.306% to about 0.374% menthol and about 0.6971% to about 0.8519% eucalyptol is clinically effective in inhibiting gingivitis. More preferably a dentifrice according to the present invention contains about 0.5112% thymol, about 0.5160% methyl salicylate, about 0.34% menthol and about 0.7745% eucalyptol and is clinically effective in inhibiting gingivitis.

Fluoride-releasing compounds may be used in the dentifrice compositions of the present invention. These compounds may be fully or slightly water soluble, release fluoride ions or fluoride-containing ions in water and do not react with other components in the composition. It is well known that dentifrice compositions containing fluoride-releasing compounds help prevent dental caries. Typical fluoride-releasing compounds are inorganic fluoride salts such as water-soluble alkaline earth metal, alkali metal, and heavy metal salts. Sodium monofluorophosphate, sodium fluoride, stannous fluoride and mixtures of these compositions are preferred.

The amount of fluoride-releasing compound present in the dentifrice compositions of this invention must be nontoxic. The specific amount depends upon the type of fluoride-releasing compound employed, the solubility of the fluoride-releasing compound and the formulation of the dentifrice composition. In general, the fluoride-releasing compound will be present in an amount by weight of up to about 1.2% w/w, preferably from about 0.1% w/w to about 1.0% w/w, and most preferably from about 0.175% w/w to about 0.8% w/w of the dentifrice composition so as to provide 800–1500 ppm $F^-$.

Surfactants or surface active agents are organic compounds that reduce surface tension between liquids and aid in the dispersion of a composition throughout the oral cavity. The surfactant in the present invention may be anionic, nonionic, or amphoteric. The oral hygiene or dentifrice compositions of the present invention may contain surfactants in amounts up to about 5.0% w/w; preferably from about 0.1% w/w to about 3.0% w/w of the dentifrice composition; and most preferably from about 0.2% w/w to about 2.0% w/w of the dentifrice composition.

The most preferred surfactants are anionic. These anionic surfactants include, but are not limited to, sodium lauryl sulfate, sodium lauroyl sarcosinate, sodium methyl cocoyl taurate, and disodium lauryl sulfosuccinate. A preferred surfactant is sodium lauryl sulfate. The compositions according to the present invention are substantially free from one or more highly pure alkali metal salts of dodecyl sulphate having less than 5% non-dodecyl alkyl sulphate salts.

Amphoteric surfactants have the capacity to behave as either an acid or a base and include quaternized imidazole derivatives. Preferred amphoteric surfactants include long chain (alkyl) amino-alkylene aklylated amine derivatives, also known as MIRANOL®, manufactured by Rhone-Poulanc, Cranberry, N.J.

Natural and artificial sweeteners may be used in the dentifrice compositions. The sweetener may be selected from a wide range of well known materials including naturally occurring water-soluble sweeteners, artificial water-soluble sweeteners and modified water-soluble sweeteners derived from naturally occurring water-soluble sweeteners. Artificial water-soluble sweeteners include, but are not limited to, soluble saccharin salts, e.g., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin and dipeptide based sweeteners, such as L-aspartic acid derived sweeteners. Dipeptide sweeteners include L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenylglycine, L-aspartyl-2,5-dihydro-L-phenylalanine and L-aspartyl-L-(1-cyclohexene)-alanine. Naturally occurring water-soluble sweeteners include, but are not limited to, sugar alcohols, including sorbitol as 70% sorbitol solution, mannitol, xylitol, maltitol, hydrogenated starch hydrolysates and mixtures thereof.

Water-soluble sweeteners derived from naturally occurring water-soluble sweeteners include, but are not limited to, chlorinated derivatives of sucrose, known, for example, under the product designation of Sucralose; and protein-based sweeteners such as thaumaoccous danielli (Thaumatin I and II).

Sorbitol solution supplies sweetness and body to the composition and gives a desirable mouth feel. Sorbitol solution also enhances flavor, prevents harsh taste and provides a fresh and lively sensation in the mouth. It also prevents caking of the dentifrice.

In general, an effective amount of sweetener is utilized to provide the level of sweetness desired in any particular embodiment of the dentifrice compositions according to the present invention. This amount will vary with the sweetener selected and the final form of the composition. The amount of sweetener normally present is from about 0.0025% w/w to about 60% w/w of the dentifrice composition. The exact range of amounts for each type of sweetener in a dentifrice is readily determined by those skill in the art.

The flavors that may be used in the invention include natural and artificial flavors known in the dentifrice art. Suitable flavors include, but are not limited to, mints, such as peppermint, citrus flavors such as orange and lemon, artificial vanilla, cinnamon, various fruit flavors, and the like. Anethole (or anise camphor, p-propenyl anisole) is a flavor constituent of anise and fennel oils that are used widely as flavoring agent and antiseptic and was found useful in masking the harsh taste of thymol.

The amount of flavor is normally a matter of preference subject to the type of final dentifrice composition, the individual flavor employed and the strength of flavor desired. The flavors are preferably utilized in amounts that may range from about 0.01% w/w to about 6% w/w of the dentifrice composition. The flavors used in the compositions according to the present invention comprise flavoring oils that are not substantially free of terpenes.

Coloring agents are used in amounts effective to produce a dentifrice of the desired color. These coloring agents may be incorporated in amounts up to about 3% by weight of the dentifrice composition. The coloring agents may also include natural food colors and dyes suitable for food, drug and cosmetic applications. These coloring agents are known as FD & C dyes and lakes. The coloring materials are preferably water-soluble. Illustrative nonlimiting examples include the indigoid dye known as FD & C Blue No. 1, and D & C Yellow No. 10. A full recitation of all FD & C colorants and their corresponding chemical structures may be found in the Kirk-Othmer Encyclopedia of Chemical Technology, 3rd Edition, in volume 5 at pages 857–884. A preferred opacifier, titanium dioxide, may be incorporated in amounts up to about 2.0% w/w, preferably less than about 1.0% w/w of the composition and most preferably less than about 0.4% w/w.

Suitable humectants in this invention include sorbitol, as 70% sorbitol solution, glycerin, propylene glycol, polyethylene glycol, mixtures thereof, and the like. Humectants may be present in amounts from about 1.0% to about 75.0% by weight of the dentifrice composition.

Suitable abrasive substances for use in this invention must be compatible with the low pH of the composition and include hydrated silica, alumina or alkali metal meta-phosphates. Silica abrasives in the dentifrice composition according to this invention may include among others, ZEODENT® (113), manufactured by J. M. Huber Corp. and SYLOID® or SYLODENT®, manufactured by W.R. Grace Co. These polishing agents may be used in amounts up to about 75.0% w/w of the composition, preferably in amounts from about 5.0% w/w to about 40% w/w of the composition and most preferably from about 5.0% w/w to about 30.0% w/w of the composition.

The dentifrice composition includes an oral vehicle that can be a paste, gel, powder or liquid. Depending upon the specific form of the dentifrice, the composition may also include binders or gelling agents to provide a desired consistency. Gelling agents such as hydroxyethyl cellulose, carboxymethyl cellulose, methyl cellulose, xanthan gum, gelling silicas and the like may be used singly or in combination. The preferred gelling system is a mixture of carboxy methyl cellulose, xanthan gum and gelling silica. Gelling agents may be used in amounts from about 0.5% w/w to about 30% w/w, preferably from about 5.0% w/w to about 15.0% w/w of the dentifrice composition, and most preferably from about 7.0% w/w to about 20% w/w of the composition.

The dentifrice composition of this invention may also contain a desensitizing agent such as strontium chloride, potassium nitrate or sodium citrate-citric acid, which may be used in an amount from about 0.5% w/w to about 10% w/w.

Suitable preservatives include benzoic acid, butylated hydroxyanisole (BHA), butylated hydroxytoluene (BHT), ascorbic acid, methyl paraben, propyl paraben, tocopherols and mixtures thereof. Preservatives when used are generally present in amounts up to about 1.0% w/w, and preferably from about 0.1% w/w to about 1.0% w/w of the dental gel composition.

The present invention is further illustrated by the following non-limiting examples. All parts and percentages in the examples and throughout the specification and claims are by weight of the final composition unless otherwise specified.

EXAMPLES 1–2 AND COMPARATIVE EXAMPLE 1

Dentifrice compositions were formulated with the ingredients listed in Table 1.

TABLE 1

| FORMULA NUMBER | Example 1 | Example 2 | Comparative Example 1 |
| --- | --- | --- | --- |
| PH | 4.5 | 4. | 7.0 |
| THYMOL | 0.5112 | 0.5112 | 0 |
| METHYL SALICYLATE | 0.5160 | 0.5160 | 0 |
| MENTHOL | 0.3400 | 0.3400 | 0 |
| EUCALYPTOL | 0.7745 | 0.7745 | 0 |
| GLYCERIN | 6.0000 | 6.0000 | 15.0 |
| SORBITOL (70%) | 40.0000 | 40.0000 | 47.0 |
| WATER | 22.4910 | 23.4910 | Q.S. |
| PEG 1450 | 3.0000 | 3.0000 | 0 |
| XANTHAN GUM | 0.2500 | 0.2500 | 0.3 |
| Na CMC | 1.2000 | 1.2000 | 0 |
| FLAVOR | 0.2250 | 0.2250 | 1.8 |
| SODIUM MFP | 0.760 | 0.760 | 0.76 |
| Na SACCHARIN | 1.2000 | 1.2000 | 0.2 |
| $NaH_2PO_4$ | 0.25 | 0.25 | 0 |
| $Na_2HPO_4$ | 0.0300 | 0.0300 | 0 |
| ZINC CITRATE | 2.0 | 1.0 | 2.0 |
| $TiO_2$ | 0.3500 | 0.3500 | |
| GELLING SILICA | 11.0 | 11.0 | 20.0 |
| ABRASIVE SILICA | 7.0 | 7.0 | 0 |
| SLS | 1.5 | 1.5 | 1.5 |
| PHOSPHORIC ACID | .45 | .45 | |

TABLE 1-continued

| FORMULA NUMBER | Example 1 | Example 2 | Comparative Example 1 |
| --- | --- | --- | --- |
| BENZOIC ACID | 0.15 | 0.15 | |
| COLOR | 0.0022 | 0.0022 | 0.004 |

Bio-Availability Studies

The bioavailability of the zinc in the compositions according to the present invention were measured using the following method. Bioavailability is the amount of zinc ion present in a dentifrice slurry after 60 seconds of mixing. This approximates the amount of time the average person applies a dentifrice composition to the teeth by brushing.

Test Slurries:

For each dentifrice, a 1:3 dentifrice-water slurry is made by adding 12 g of double deionized water to 4 g of dentifrice in a 30 ml flat bottomed test tube and dispersing for 60 seconds by vortexing or using an airless mixing device. Aliquots of the slurries are immediately placed in plastic Eppendorf microcentrifuge tubes and centrifuged at 12,000 rpm. Aliquots of the supernatant are removed by pipet without disturbing the pellet, and immediately measured for available zinc as described below.

Available Zinc Analysis:

A sample of each solution is diluted with appropriate solution and the zinc content determined by comparison to a similarly prepared standard curve. A Perkin-Elmer AA Spectrophotometer 3030 equipped with zinc hollow cathode lamp is used for the determination of zinc content in the solutions. The results are presented in Table 2.

TABLE 2

| | Zinc Citrate Content | Total Zinc Amount | Bioavailable Zinc Amount |
| --- | --- | --- | --- |
| Comparative Example | 2% | 6,200 ppm | 1,550 ppm |
| Example 1 | 2% | 6,200 ppm | 2,170 ppm |
| Example 2 | 1% | 3,100 ppm | 1,550 ppm |

As can be seen in the results listed in TABLE 2, Example 1 delivered approximately 30% more zinc that the comparative example even though it had the same amount of zinc. Additionally, Example 2, which has half the amount of zinc as the comparative example, was able to deliver the same amount of zinc as the comparative example.

Both animal and clinical studies were conducted to determine the amount of calculus reduction.

Rat Calculus

The rat studies were conducted by applying each composition to the teeth of individual rats with a cotton swab each morning and afternoon for 5 days a week for a three-week period. The calculus formation was scored according to the method of Francis and Briner, Journal of Dental Research, Vol. 48, 1185–1195 (1969). The results were presented in Table 3. The results of the rat calculus study indicate that the formulation of this invention (i.e. example 2) was effective at reducing calculus formation even when only 1% zinc citrate is present.

Human Clinical Calculus Study

The dentifrice compositions according to examples 1 and 2 were tested for calculus inhibition in a clinical study. This study consisted of the following stages:

1. Participants undergo a thorough dental cleaning to remove all tartar
2. Participants then use the test placebo, Crest® Regular, for three months
3. Participants are evaluated and scored on level of tartar buildup, then separated into 3 balanced treatment group
4. Participants undergo a second dental cleaning to remove all tartar
5. Participants use either the 1% ZCT, 2% ZCT or placebo products for three months
6. Participants are evaluated and scored again on level of tartar buildup using the Volpe Manhold method.

The results were also presented in Table 3. The clinical results indicate that the formulation of this invention (i.e. example 2) provides excellent calculus inhibition even with only 1% zinc citrate present in the formula.

TABLE 3

|  | Bioavailable Zinc Amount | Calculus reduction (rat) | Calculus reduction (Human) |
| --- | --- | --- | --- |
| Comparative Example | 1,550 ppm | 15% | 32% |
| Example 1 | 2,170 ppm | 15% | 29% |
| Example 2 | 1,550 ppm | 15% | 26% |

As can be seen in the results listed in TABLE 3, Example 2, which delivers the same amount of bioavailable zinc as the comparative example, was able to achieve parity calculus reduction as the comparative example.

As the invention has been described in detail and with reference to specific examples thereof, it will be apparent to one skilled in the art that various changes and modifications can be made therein without departing from the spirit and scope thereof.

What is claimed is:

1. A dentifrice composition comprising:

zinc citrate, a buffer system, an abrasive; and an oral vehicle, wherein the dentifrice composition has a pH from about 3.0 to about 5.5, the zinc citrate is in an amount sufficient to provide at least about 2000 ppm of zinc ion and the amount of zinc ion that is bioavailable is at least about 1000 ppm.

2. The dentifrice composition according to claim 1 wherein the pH is about 4.5.

3. The dentifrice composition according to claim 1 wherein the buffer system comprises an acid and at least one corresponding salt.

4. The dentifrice composition according to claim 3 wherein the acid and the corresponding salt are selected from the group consisting of citric acid-sodium citrate, phosphoric acid-sodium phosphate, sodium monobasic phosphate and sodium dibasic phosphate, acetic acid-sodium acetate, succinic acid-sodium succinate, aconitic acid-sodium aconitate and benzoic acid-sodium benzoate.

* * * * *